(12) United States Patent
Kimle et al.

(10) Patent No.: US 12,091,647 B2
(45) Date of Patent: Sep. 17, 2024

(54) MOVING BED BIOFILM REACTOR SYSTEM FOR PRODUCTION OF ALGAE BIOMASS

(71) Applicant: Kimle Aquaculture, LLC, Slater, IA (US)

(72) Inventors: Jackson Kimle, Ames, IA (US); Matthew Ellis, Ames, IA (US)

(73) Assignee: KIMLE AQUACULTURE, LLC, Ames, IA (US)

( * ) Notice: Subject to any disclaimer, the term of this patent is extended or adjusted under 35 U.S.C. 154(b) by 520 days.

(21) Appl. No.: 17/195,077

(22) Filed: Mar. 8, 2021

(65) Prior Publication Data

US 2021/0277344 A1    Sep. 9, 2021

Related U.S. Application Data

(60) Provisional application No. 62/986,879, filed on Mar. 9, 2020.

(51) Int. Cl.
| | |
|---|---|
| *C12M 1/00* | (2006.01) |
| *C12M 1/12* | (2006.01) |
| *C12M 1/26* | (2006.01) |

(52) U.S. Cl.
CPC .......... *C12M 21/12* (2013.01); *C12M 25/20* (2013.01); *C12M 33/14* (2013.01)

(58) Field of Classification Search
CPC ...... C12M 21/12; C12M 25/20; C12M 33/14; C12M 23/58; C12M 21/02; C12N 5/0075
See application file for complete search history.

(56) References Cited

U.S. PATENT DOCUMENTS

| | | |
|---|---|---|
| 3,598,726 A | 8/1971 | Welch |
| 4,324,068 A | 4/1982 | Anthony |
| 5,647,983 A | 7/1997 | Limcaco |
| 6,158,386 A | 12/2000 | Limcaco |
| 6,667,171 B2 | 12/2003 | Bayless et al. |

(Continued)

FOREIGN PATENT DOCUMENTS

| | | |
|---|---|---|
| CN | 103289887 | 9/2013 |
| WO | 2010011320 | 1/2010 |

(Continued)

OTHER PUBLICATIONS

Tsioptsias, C., et al., "Enhancement of the performance of a combined microalgae-activated sludge system for the treatment of high strength molasses wastewater", 2016, J. Environmental Management, vol. 183, Part 1, pp. 126-132. (Year: 2016).*

(Continued)

*Primary Examiner* — Elizabeth A Robinson
*Assistant Examiner* — Jonathan E Lepage
(74) *Attorney, Agent, or Firm* — BrownWinick Law Firm; Christopher A. Proskey

(57) ABSTRACT

A moving bed biofilm reactor system for growing microorganisms comprising a reservoir containing a fluid that contains nutrients conducive to growth of microorganisms and a plurality of inert biomass carriers having a surface area configured to support growth of microorganisms is provided. The microorganisms may be used to remove a pollutant from a fluid. Furthermore, the microorganisms may be harvested and used as a foodstuff fertilizer, biofuels, and bioplastics.

21 Claims, 6 Drawing Sheets

(56) References Cited

U.S. PATENT DOCUMENTS

| | | |
|---|---|---|
| 6,794,184 B1 | 9/2004 | Mohr |
| 7,189,323 B2 | 3/2007 | Lofqvist et al. |
| 8,372,631 B2 | 2/2013 | Shepherd |
| 8,377,687 B2 | 2/2013 | Shepherd |
| 9,932,549 B2 | 4/2018 | Gross et al. |
| 11,225,424 B2 | 1/2022 | Kimle et al. |
| 2009/0035848 A1 | 2/2009 | Hickey |
| 2010/0144017 A1 | 6/2010 | Shepherd |
| 2010/0224574 A1 | 9/2010 | Youngs et al. |
| 2010/0267122 A1 | 10/2010 | Chinnasamy et al. |
| 2011/0070632 A1 | 3/2011 | Katoch et al. |
| 2011/0217764 A1 | 9/2011 | Christenson et al. |
| 2011/0258915 A1 | 10/2011 | Subhadra |
| 2011/0263886 A1 | 10/2011 | Kale |
| 2011/0312062 A1 | 10/2011 | Nordvik et al. |
| 2011/0283608 A1 | 11/2011 | Patel et al. |
| 2012/0252105 A1 | 10/2012 | Ahrens et al. |
| 2013/0020266 A1 | 1/2013 | Timmons et al. |
| 2014/0273171 A1 | 9/2014 | Gross et al. |
| 2014/0273174 A1 | 9/2014 | Gross et al. |
| 2016/0289107 A1* | 10/2016 | Seidl .................. C02F 3/30 |

FOREIGN PATENT DOCUMENTS

| | | | |
|---|---|---|---|
| WO | 2010030953 | 3/2010 | |
| WO | WO-2010048525 A2 * | 4/2010 | ............ C12M 21/02 |

OTHER PUBLICATIONS

"AnoxKaldnes(TM) MBBR", Veolia Water Technologies Communications, Singapore, Aug. 2014, 4 pages. (Year: 2014).*

International Search Report for International Application No. PCT/US2014/029618 Aug. 21, 2014.

Bitog et al., "Application of computational fluid dynamics for modeling and designing photobioreactors for microalgae production: A review," Computers and Electronics in Agriculture (2011), 76: 131-147. Jan. 24, 2011.

Christenson et al., "Rotating Algal Biofilm Reactor and Spool Harvester for Wastewater Treatment with Biofuels By-Products." Biotechnology and Bioengineering, DOI 10.1002/bit.24451 (2012) Wiley Periodicals, Inc. Jan. 20, 2012.

Johnson et al., "Development of an attached microalgal growth system for biofuel production," Applied Microbiology and Biotechnology (2010), 85:525-534 Jul. 7, 2009.

* cited by examiner

MOVING BED BIOFILM REACTOR SYSTEM FOR PRODUCTION OF ALGAE BIOMASS

CROSS REFERENCE TO RELATED APPLICATIONS

This patent application claims priority to U.S. Provisional Patent Application No. 62/986,879 filed on Mar. 9, 2020, the entirety of which is incorporated herein fully by reference.

FIELD OF THE DISCLOSURE

This disclosure relates generally to a system for treatment of a fluid and for producing microorganisms, and in particular to a system for producing algae biomass. In one arrangement, the disclosure relates to a method of producing microorganisms, such as algae biomass, using a moving bed biofilm reactor (MBBR) system, also referred to as a bioreactor system in this disclosure. The microorganisms produced by the system may be used to remove a pollutant from a fluid utilized in a system, such as a recirculating aquaculture system, by exposing the microorganisms to a fluid containing a pollutant in which the microorganisms uptake the pollutant, then exposing the microorganisms to a condition in order to stimulate the microorganisms to release the pollutant.

BACKGROUND OF THE DISCLOSURE

There is a rising demand for improvements in treatment of fluids, especially fluids utilized in aquaculture systems. Currently, treatment of fluid occurs through many different unit processes. The different treatment processes utilized to remove pollutants from the fluid are capital intensive and require significant operating cost. Additionally, many different processes are needed in order to remove pollutants including, but not limited to, fecal matter, uneaten food, Nitrogen (N), Phosphorous (P), Potassium (K), Carbon (C), ammonia ($NH_3$), carbon dioxide ($CO_2$), toxic metals, salts, pharmaceuticals, or hormones. Furthermore, the current processes available to remove these pollutants do not provide the opportunity to capture these pollutants, which can be utilized for numerous purposes, but the current processes only remove them.

Aquaculture systems have large volumes of waste discharge which results in a significant challenge as fish producers are required to invest in more capital intensive waste treatment in order to meet tightening discharge requirements. This results in lowering feasibility and profitability of investments in aquaculture systems.

Utilizing a microorganism growing apparatus in connection with a recirculating aquaculture system provides the ability for microorganisms to consume dissolved pollutants and harvest them as a by-product. Since microorganisms such as algae can consume Nitrogen (N), Phosphorous (P), Potassium (K), Carbon (C), ammonia ($NH_3$), carbon dioxide ($CO_2$), toxic metals, salts, pharmaceuticals, and hormones in one process, rather than multiple processes, this simplifies and increases efficiency of aquaculture systems.

MBBR is commonly used as one step of a wastewater treatment process. The MBBR process takes place in a basin, also called a reactor or aeration tank. The basin is open or closed at the top, exposing the water in the basin to open air. The basin is full of small inert plastic pieces called media or carriers that provide surface area for microorganisms to grow on them. The carriers have similar density to the fluid contained in the basin so the carriers will mix throughout the fluid rather than floating or sinking. An aeration grid located in the basin circulates the fluid and carriers. A sieve located at the outlet of the basin prevents the carriers from escaping from the basin when the fluid is removed from the basin. The microorganisms attached to the carriers consume pollutants contained in the fluid. The fluid can then be removed from the basin; thus the pollutant is removed from the fluid.

While MBBR may be used to remove pollutants from a fluid, the microorganisms must first be produced. Cultivating the microorganisms on the carriers remains a challenge. In particular, providing adequate sunlight, carbon dioxide, and nutrients is necessary for the cultivation of the microorganisms. All MBBR systems to date have used no light source. Rather than producing photosynthetic microorganisms, bacteria that need a dark environment have been produced.

For the reasons stated above, and for other reasons which will become apparent to those skilled in the art upon reading and understanding the specification, there is a need in the art for an improved fluid treatment system and an improved method of producing algae and other microorganisms for removal of a pollutant from a fluid.

Thus it is a primary object of the disclosure to provide a method of producing microorganisms to remove a pollutant from a fluid that is efficient.

Yet another object of the disclosure is to provide a method of producing microorganisms to remove a pollutant from a fluid utilized in a system that is simple in design.

Another object of the disclosure is to provide a method of producing microorganisms to remove a pollutant from a fluid that is inexpensive.

Another object of the disclosure is to provide a method of producing microorganisms to remove a pollutant from a fluid that has a smaller footprint than other biological systems.

Yet another object of the disclosure is to provide a method of producing microorganisms to efficiently and effectively remove a pollutant from effluent.

Another object of the disclosure is to provide a method of producing microorganisms to remove a pollutant from a fluid that has a high pollutant removal rate.

Another object of the disclosure is to provide a method of producing microorganisms to remove a pollutant from a fluid utilized in a recirculating aquaculture system that maximizes production of fish on a limited supply of water.

Yet another object of the disclosure is to provide a method of producing microorganisms to remove a pollutant from a fluid utilized in a recirculating aquaculture system that maximizes production of fish on a limited supply of land.

Another object of the disclosure is to provide a method of producing microorganisms to remove a pollutant from a fluid utilized in a recirculating aquaculture system that allows for disease control.

Yet another object of the disclosure is to provide a method of producing microorganisms to remove a pollutant from a fluid utilized in a recirculating aquaculture system that allows for control of the environment in order to maximize fish growth.

Another object of the disclosure is to provide a method of producing microorganisms to remove a pollutant from a fluid utilized in municipal wastewater treatment.

Yet another object of the disclosure is to provide a method of producing microorganisms to remove a pollutant from a fluid utilized in industrial wastewater treatment.

These and other objects, features, or advantages of the present disclosure will become apparent from the specification and claims.

BRIEF SUMMARY OF THE DISCLOSURE

The disclosure relates to a bioreactor system comprising a microorganism growing apparatus and a method of using microorganisms to remove a pollutant from a fluid utilized in a system. The disclosure relates to a method of using microorganisms, including, but not limited to, bacteria, fungi, or algae, to remove a pollutant from a fluid utilized in a system. Furthermore, the disclosure relates to a method of using microorganisms, including, but not limited to, bacteria, fungi, archaea, protozoa/metazoan or algae, to remove a pollutant from a fluid used in a system utilizing a microorganism growing apparatus. Furthermore, the disclosure relates to a method of using microorganisms to remove a pollutant from a fluid used in a system utilizing a microorganism growing apparatus wherein the microorganisms are exposed to a first fluid containing a pollutant wherein the microorganisms are exposed to a first condition, exposing the microorganisms to light and air (which may be a $CO_2$-rich gaseous phase or an $O_2$-rich gaseous phase, among other compositions), and then exposing the microorganisms to a second fluid wherein the microorganisms are exposed to a second condition and the microorganisms are stimulated to release the pollutant.

BRIEF DESCRIPTION OF THE DRAWINGS

The figures depict one or more embodiments of a bioreactor system. Furthermore, the figures depict one or more embodiments of a bioreactor system.

DETAILED DESCRIPTION

Figure 1:
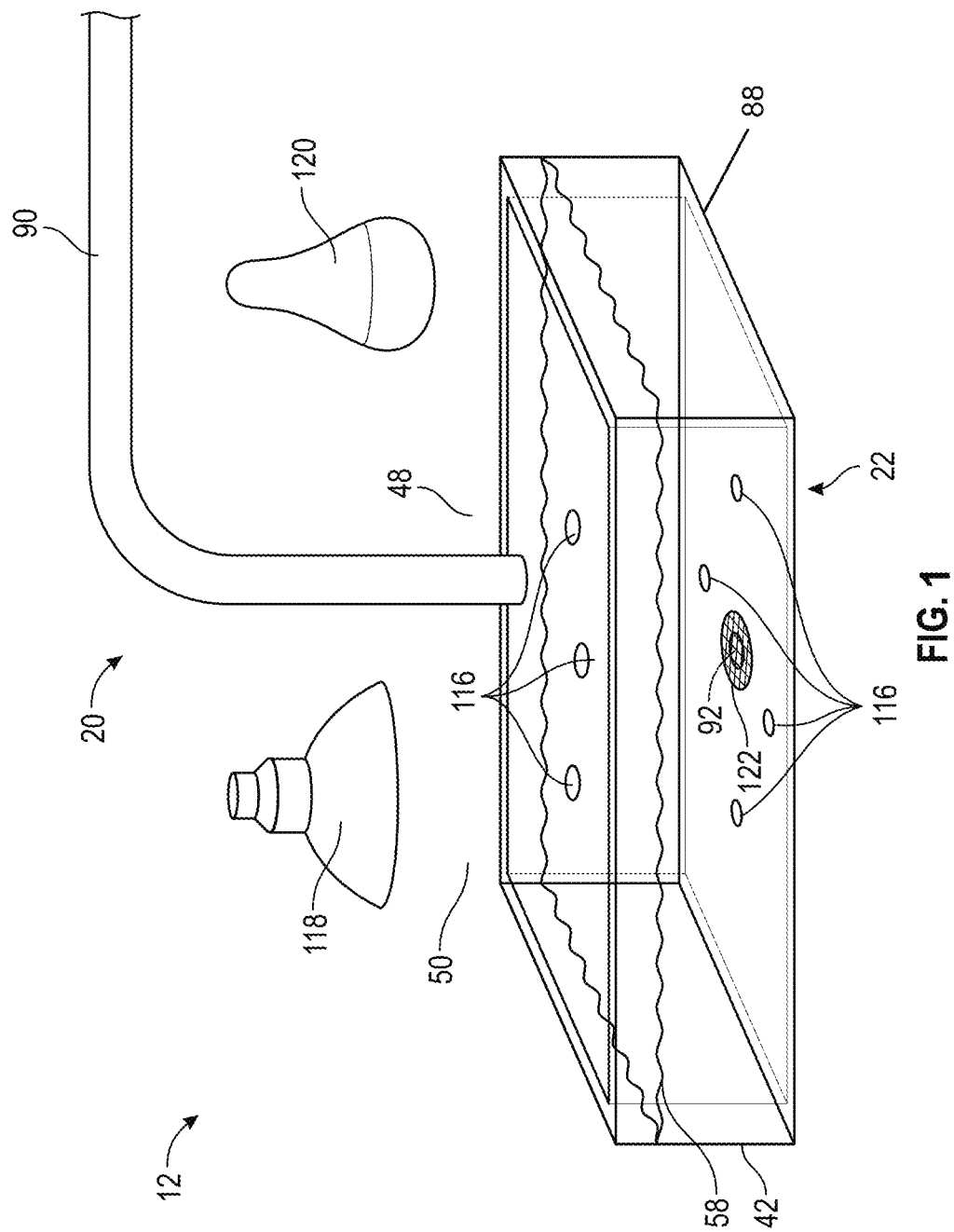
FIG. 1 depicts a perspective view of a moving bed biofilm reactor for producing microorganisms according to one embodiment.
Figure 2:
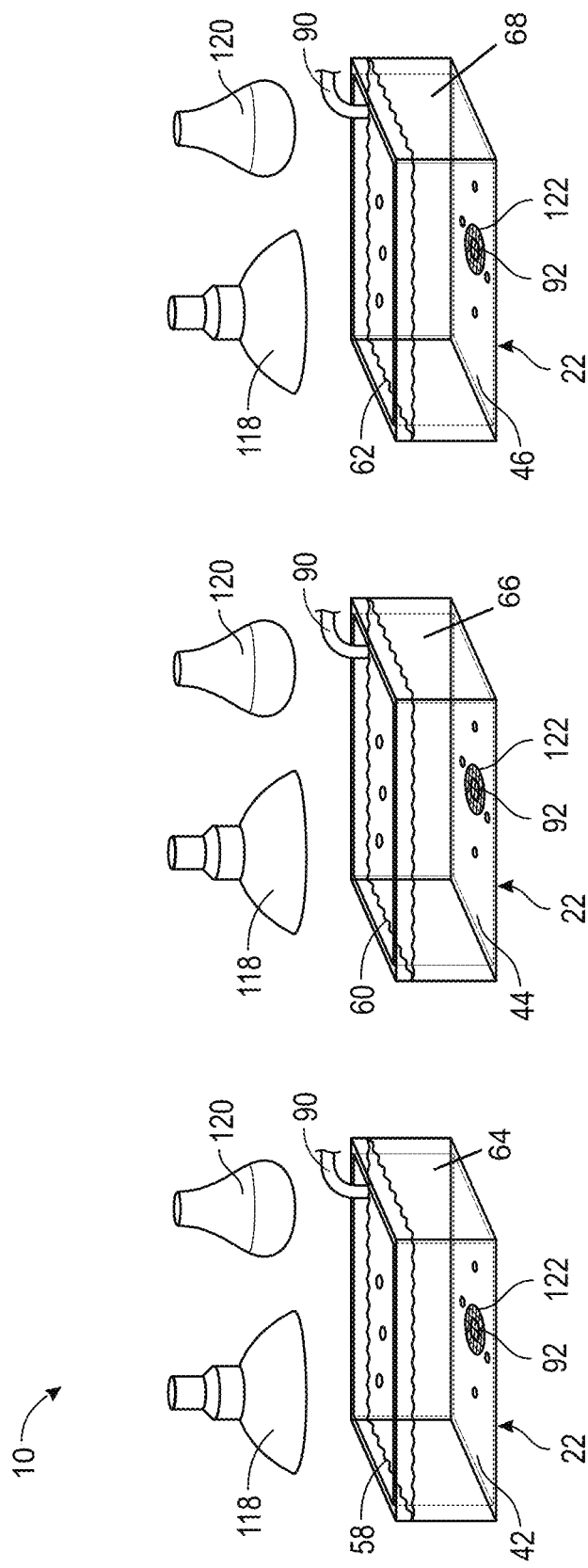
FIG. 2 depicts a perspective view of a bioreactor system using microorganisms to remove pollutants from a fluid according to one embodiment.

In the following detailed description of the embodiments, reference is made to the accompanying drawings which form a part hereof, and in which is shown by way of illustration specific preferred embodiments in which the disclosure may be practiced. These embodiments are described in sufficient detail to enable those skilled in the art to practice the disclosure, and it is to be understood that other embodiments may be utilized and that mechanical, procedural, and other changes may be made without departing from the spirit and scope of the present disclosures. The following detailed description is, therefore, not to be taken in a limiting sense, and the scope of the present disclosure is defined only by the appended claims, along with the full scope of equivalents to which such claims are entitled.

As used herein, the terminology such as vertical, horizontal, top, bottom, front, back, end and sides are referenced according to the views presented. It should be understood, however, that the terms are used only for purposes of description, and are not intended to be used as limitations.

Accordingly, orientation of an object or a combination of objects may change without departing from the scope of the disclosure.

A Bioreactor System

In the arrangement shown, as one example, a bioreactor system 10 using microorganisms 84 to remove pollutants from a fluid 58 (or simply "recirculating aquaculture system" 10 or "system" 10) is formed of any suitable size, shape, and design and is configured to be utilized in association with any type of microorganism growing apparatus 12. The system 10 is utilized for many purposes including, but not limited to, treatment of a fluid 58, treatment of wastewater, rearing of aquatic animals and/or the cultivation of aquatic plants where fluid 58 exchange is limited. Furthermore, the system 10 may be utilized for rearing of aquatic animals including vertebrate or invertebrate. The system 10 may be utilized for any purpose or objective without departing from the scope of the disclosure. In one arrangement, as one example, the system 10 may be utilized for fish production where exchange of fluid 58 is limited. In this arrangement, the system 10 treats the fluid 58 by removing pollutants in order for the fluid 58 to be recirculated throughout the system 10. This provides the ability to maintain clean fluid 58 and to provide a suitable habitat for fish growth and health. In one arrangement, as one example, the system 10 comprises at least one tank 88, a radial flow settler, a first header tank, a Low Head Oxygenator (LHO), a foam fractionator, a sump pump, a drum filter, a waterfall, a microorganism growing apparatus 12, a second header tank, and a fluid recirculation system.

As stated above, in one arrangement, as one example, the system 10 comprises a microorganism growing apparatus 12 in order to provide for filtering a fluid 58 which is recirculated throughout the system 10. This allows for the fluid 58 to be reused within the system 10 while controlling the environment in order to maximize fish growth and production. In one arrangement, as described in more detail below, the fluid 58 moves from the drum filter of the system 10 to the microorganism growing apparatus 12 through a waterfall.

The system 10 may be formed of any suitable size, shape, and design. The system 10 may be formed of any material that is acceptable for treatment of a fluid. Furthermore, the system 10 may be formed of any material that is acceptable for fish production. The system 10 may be formed of any material without departing from the scope of the disclosure.

Plurality of Tanks

In one arrangement, as one example, the system 10 comprises at least one tank 88. In another arrangement, the system 10 comprises a plurality of tanks 88. However, any number of tanks 88 may be used without departing from the scope of the disclosure. For example, the system 10 may comprise one, two, three, four, five, six, seven, eight, nine, ten, or more tanks 88 without departing from the scope of the disclosure. Tanks 88 may be formed of any suitable size, shape and design and are configured to hold and/or supply water and/or other components for operation of the system 10. The at least one tank 88 is configured to hold a fluid 58 among other components including, but not limited to, aquatic animals or aquatic plants. The at least one tank 88 is configured to hold a fluid 58 and any other component without departing from the scope of the disclosure. In one arrangement, as one example, the at least one tank 88 is configured to hold a fluid 58 and fish in order to facilitate efficient fish production.

Each tank 88 utilized in the system 10 may comprise, among other components, an inlet 90, a center drain 92, and a sidewall drain 94. Furthermore, the tanks 88 are formed of any suitable, size, shape, and design. In one arrangement, the tanks 88 are circular in shape with smooth walls and a sloping bottom in order to facilitate in waste concentrating at the bottom and exiting out the center drain 92.

Inlet

In the arrangement shown, as one example, the system 10 comprises at least one tank 88. Each tank 88 utilized in the system 10 may comprise, among other components, an inlet 90 wherein a fluid 58/60/62 enters the tank 88. Inlet 90 may be formed of any suitable size, shape and design and is configured to provide a path for water into the system 10. In the arrangement shown, as one example, the inlet 90 may be located at any position on the outer perimeter of the tank 88 without departing from the scope of the disclosure. As previously stated, the system 10 comprises, among other components, a fluid recirculation system. The inlet 90 is connected to at least one of the fluid recirculation system which allows fluid 58 to flow into the tank 88. The inlet 90 may be formed of any suitable size, shape, and design. Furthermore, the inlet 90 may be formed of any material that is acceptable for entry of a fluid 58. In one arrangement, as one example, the inlet 90 is formed of a fluid recirculation system, a tube, a filter, a mesh filter, etc. The inlet 90 may be formed of any material without departing from the scope of the disclosure.

Center Drain

In the arrangement, as one example, the system 10 comprises at least one tank 88. Each tank 88 utilized in the system 10 may comprise, among other components, a center drain 92. Center drain 92 may be formed of any suitable size, shape and design and is configured to provide a path for water out of the system 10. In the arrangement shown, as one example, the center drain 92 allows fluid 58 to exit the tank 88 through the center of the tank 88. The center drain 92 may be formed of any material that is acceptable for a fluid 58 to exit a tank 88. Furthermore, the center drain 92 may be formed of any material that is acceptable for a fluid 58 to exit a tank 88. The center drain 92 may be formed of any material without departing from the scope of the disclosure.

Sidewall Drain

In the arrangement shown, as one example, the system 10 comprises at least one tank 88. In the arrangement shown, as one example, each tank 88 utilized in the system 10 may comprise, among other components, a sidewall drain 94. Sidewall drain 94 may be formed of any suitable size, shape and design and is configured to facilitate a path for water to escape the system 10. In the arrangement shown, as one example, the sidewall drain 94 allows fluid 58/60/62 to exit the tank 88 through the side of the tank 88. The sidewall drain 94 may be formed of any material that is acceptable for a fluid 58/60/62 to exit a tank 88. Furthermore, the sidewall drain 94 may be formed of any material that is acceptable for a fluid 58/60/62 to exit a tank 88. The sidewall drain 94 may be formed of any material without departing from the scope of the disclosure.

Radial Flow Settler

As provided above, the system 10 comprises, among other components, at least one radial flow settler. The radial flow settler is a passive filtration device that removes waste including, but not limited to, solid waste, from the system 10. Any number of radial flow settlers may be used in the system 10 without departing from the scope of the disclosure. For example, the system 10 may comprise one, two, three, four, five, six, seven, eight, nine, ten, or more radial flow settlers without departing from the scope of the disclosure.

Each radial flow settler utilized in the system 10 is connected to one of the fluid recirculation systems in order to filter waste from the fluid 58 utilized in the system 10. Each radial flow settler operates by utilizing gravity to move fluid 58 through the radial flow settler in order to filter waste including, but not limited to, fecal matter, uneaten food, other pollutants, etc.

The radial flow settler may be formed of any material that is acceptable for a passive filtration device. The radial flow settler may be formed of any material without departing from the scope of the disclosure. Furthermore, in one arrangement, as one example, a radial flow settler is located in close proximity to each tank 88 in order to filter pollutants from the fluid 58 being drained from the tank 88.

Header Tank

As provided above, the system 10 comprises, among other components, a header tank. The header tank is a container of fluid 58 utilized to maintain the level of pressure and fluid in the reservoir or tank below. In one arrangement, the system 10 comprises a first header tank and a second header tank. In one arrangement, the first header tank is positioned above the microorganism growing apparatus 12 in order to maintain the level of pressure and fluid in the microorganism growing apparatus 12. Also, in one arrangement, the second header tank is located above the plurality of tanks 88 in order to maintain the level of pressure and fluid in the tanks 88. The system 10 may comprise any number of header tanks without departing from the scope of the disclosure. For example, the system 10 may comprise one, two, three, etc. header tanks without departing from the scope of the disclosure. Furthermore, the header tank may be formed of any material without departing from the scope of the disclosure. Additionally, the header tank may be formed of any shape, size, or design without departing from the scope of the disclosure.

In one arrangement, as one example, fluid 58 moves from the at least one tank 88 to a first header tank via the fluid recirculation system wherein the fluid 58 moves from the first header tank to the drum filter. Also, in one arrangement, fluid 58 moves from the low head oxygenator to a second header tank to the plurality of tanks 88 through the inlet 90 after having pollutants removed from the fluid 58 throughout the system 10.

Throughout the disclosure, reference to a header tank refers to a first header tank or a second header tank, unless the disclosure specifically states that it is referring to only a specific header tank.

Low Head Oxygenator (LHO)

As provided above, in one arrangement, the system 10 comprises, among other components, a low head oxygenator (LHO). The LHO is utilized to efficiently and simply add oxygen to fluid 58 utilized in the system 10. Furthermore, the LHO is used to remove nitrogen from the fluid 58 utilized in the system 10. The LHO may be formed of any material without departing from the scope of the disclosure. Additionally, the LHO may be formed of any shape, size, or design without departing from the scope of the disclosure.

In one arrangement, as one example, the fluid 58 moves from the foam fractionator to the LHO in order to filter pollutants from the fluid 58 utilized in the system 10. In one arrangement, the fluid 58 moves from the LHO to a second header tank in order to recirculate the fluid 58 utilized in the system 10.

Foam Fractionator

As stated above, in one arrangement, the system 10 comprises, among other components, a foam fractionator. The foam fractionator is utilized to remove pollutants from the fluid 58 utilized in the system 10. The foam fractionator utilizes a chemical process wherein hydrophobic molecules are separated from the fluid 58 using rising columns of foam resulting in separating pollutants from the fluid 58.

The foam fractionator may be formed of any material that is acceptable to remove pollutants from a fluid 58 utilized in a system 10. Additionally, the foam fractionator may be formed of any shape, size, or design without departing from the scope of the disclosure.

In one arrangement, as one example, the fluid 58 moves from the sump pump to the foam fractionator in order to move the fluid 58 throughout the system 10. Furthermore, in one arrangement, the fluid 58 moves from the foam fractionator to the LHO.

Sump Pump

As provided above, in one arrangement, the system 10 comprises, among other components, a sump pump. The sump pump is utilized to remove the fluid 58 from the microorganism growing apparatus 12. The sump pump may be formed of any material that is acceptable to remove a fluid 58 from the microorganism growing apparatus 12. In one arrangement, as one example, the fluid 58 moves from the microorganism growing apparatus 12 to the sump pump wherein the fluid 58 is transferred to the foam fractionator in order to move the fluid 58 throughout the system 10. Furthermore, the sump pump may be formed of any material without departing from the scope of the disclosure. Additionally, the sump pump may be formed of any shape, size, or design without departing from the scope of the disclosure.

Drum Filter

As provided above, in one arrangement, the system 10 comprises, among other components, a drum filter. The drum filter consists of a drum rotating in a tub of fluid 58 and is utilized to filter pollutants from the fluid 58. The drum filter may be formed of any material that is acceptable to filter pollutants from the fluid 58. Additionally, the drum filter may be formed of any shape, size, or design without departing from the scope of the disclosure.

In one arrangement, the fluid 58 moves from a first header tank to the drum filter. Additionally, in one arrangement, as one example, the fluid 58 moves from the drum filter to the microorganism growing apparatus 12. In one arrangement, the fluid 58 moves from the drum filter to the microorganism growing apparatus 12 through a waterfall. However, the fluid 58 may move from the drum filter to the microorganism growing apparatus 12 via any means without departing from the scope of the disclosure.

Waterfall

In one arrangement, as one example, the system 10 comprises a waterfall. The waterfall is utilized to move the fluid 58 utilized in the system 10 from the drum filter to the microorganism growing apparatus 12 in order to filter the pollutants from the fluid 58. However, any other means of moving the fluid 58 from the drum filter to the microorganism growing apparatus 12 is contemplated by the disclosure including, but not limited to, a pipe, a tube, etc. The waterfall is formed of any shape, size, or design without departing from the scope of the disclosure.

Fluid Recirculation System

As provided above, in one arrangement, the system 10 comprises, among other components, a fluid recirculation system. The fluid recirculation system is utilized to connect the multiple components of the system 10 to one another in order to allow the fluid 58 utilized in the system 10 to move from one component to the next. In other words, the fluid recirculation system serves as the recirculation system of the system 10. The fluid recirculation system provides the system 10 with the ability to recirculate fluid 58 in order to rear aquatic animals or cultivate aquatic plants. In one embodiment, the fluid recirculation system is comprised of a plurality of pipes. However, the fluid recirculation system may be comprised of any system or apparatus that provides for the exchange or recirculation of fluid without departing from the disclosure. Throughout the disclosure, the fluid recirculation system may be referred to as "a fluid exchange system", "a plurality of pipes", "pipes", or "a recirculation system" without departing from the scope of the disclosure. In one arrangement, as one example, the fluid 58 utilized in the system 10 moves from a tank 88 to the center drain 92 or the sidewall drain 94 to a first header tank through a fluid recirculation system, then the fluid 58 moves to the first header tank to the drum filter through a fluid recirculation systems.

The fluid recirculation system may be formed of any material that is acceptable to transfer a fluid 58 from one component of the system 10 to another component. In one arrangement, the fluid recirculation system is formed of metal. Additionally, the fluid recirculation system may be formed of any shape, size, or design without departing from the scope of the disclosure.

Water Chiller

In one arrangement, as one example, the system 10 comprises at least one water chiller. The at least one water chiller is utilized to chill the fluid 58/60/62 utilized in the system 10. The at least one water chiller may be formed of any shape, size, or design without departing from the scope of the disclosure.

Solids Collection Tank

In one arrangement, as one example, the system 10 comprises at least one solids collection tank. The at least one solids collection tank is utilized to collect solids, wastes, debris, and the like in order to prevent the solids, waste, and debris from being circulated throughout the system 10. The at least one solids collection tank may be formed of any shape, size, or design without departing from the scope of the disclosure.

Targeted Pollutant Release in Microorganisms System

Figure 5:
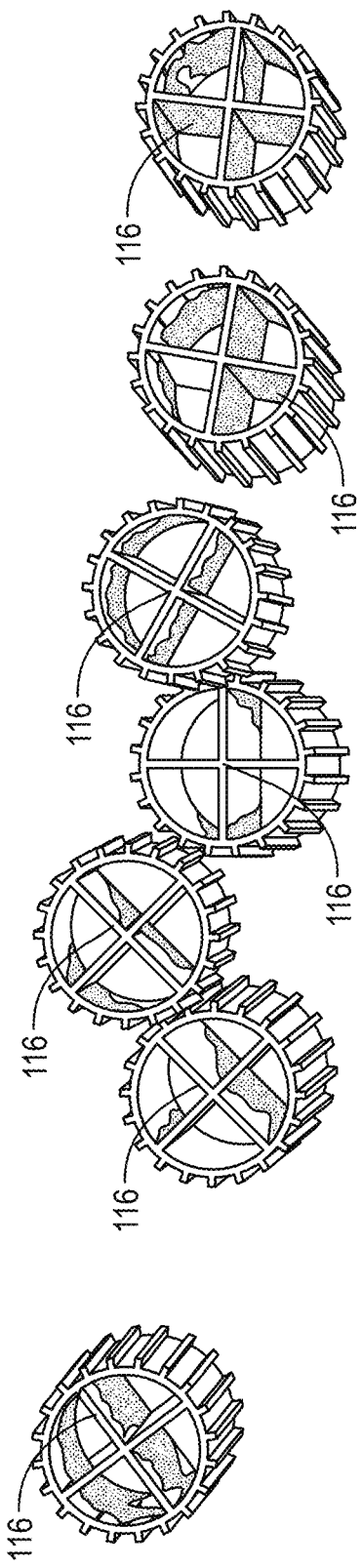
FIG. 5 depicts algae growing on carriers according to one embodiment.
Figure 6:
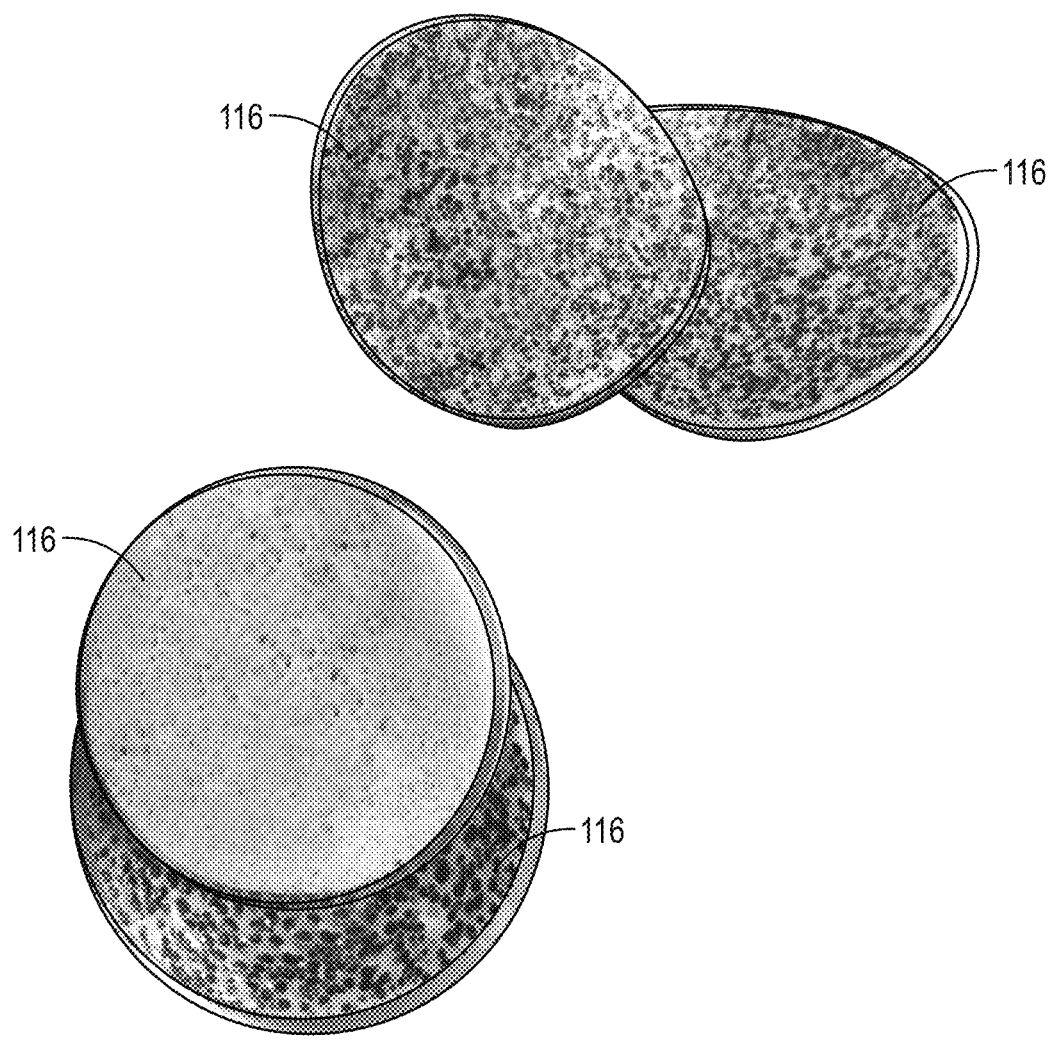
FIG. 6 depicts algae growing on carriers according to one embodiment.

In the arrangement shown, as one example, the system 10 utilizes microorganisms 84 such as bacteria, algae 52, and the like to remove a pollutant from a fluid 60. In one arrangement, the system 10 comprises a microorganism growing apparatus 12, microorganisms 84, a first reservoir 42 (or simply a "reservoir" 42), a first fluid 58 (or simply a "fluid" 58) wherein the microorganisms 84 are cultivated in fluid 58 using a plurality of inert carriers 116 on which microorganisms 84 grow and are contained. Examples of algae 52 growing on carriers 116 are shown in FIGS. 5 and 6. The system 10 further comprises a second reservoir 44 and a second fluid 60 in which the microorganisms 84 are exposed to and uptake a pollutant contained in fluid 60. The system 10 further comprises a third reservoir 46 and a third fluid 62 in which the microorganisms 84 are stimulated to release the pollutant into fluid 62. The microorganisms 84 may be moved from one reservoir 42/44/46 by removing the carriers 116 containing the microorganisms 84 from one reservoir 42/44/46 and moving the carriers 116 to another reservoir 42/44/46.

A method of removing a pollutant from a fluid 60 comprises the steps of: providing a first reservoir 42, filling the first reservoir 42 with a first fluid 58, submerging a plurality of carriers 116 in the first fluid 58 wherein at least a portion of the carriers 116 have been exposed to microorganisms 84, controlling the first fluid 58 within the first reservoir 42 to have a first condition 64 that is conducive to growing microorganisms 84, exposing the microorganisms 84 to the first fluid 58 within the first reservoir 42 wherein the microorganisms 84 are exposed to the first condition 64 and the microorganisms 84 grow and reproduce, providing a second reservoir 44, filling the second reservoir 44 with a second fluid 60 having a concentration of a pollutant; controlling the second fluid 60 within the second reservoir 44 to have a second condition 66; exposing a portion of the microorganisms 84 contained on carriers 116 to the second fluid 60 within the second reservoir 44 wherein the microorganisms 84 are exposed to the second condition 66 and the microorganisms 84 consume or uptake the pollutant from the second fluid 60, providing a third reservoir 46, filling the third reservoir 46 with a third fluid 62, controlling the third fluid 62 within the third reservoir 46 to have a third condition 68, and exposing a portion of the microorganisms 84 contained on carriers 116 to the third fluid 62 within the third reservoir 46 wherein the microorganisms 84 are exposed to the third condition 68 and the microorganisms 84 are stimulated to release the pollutant into the third fluid 62. Any number of reservoirs 42/44/46 is hereby contemplated for use.

Microorganisms

In one arrangement, as one example, the system 10 comprises a method for production of microorganism biomass comprising a reservoir 44 configured to contain a fluid 60 wherein the fluid 60 provides nutrients to the microorganisms 84 and one or more inert biomass carriers 116 having a surface area are configured to support growth of the microorganisms 84. Furthermore, the microorganisms 84 may remove a pollutant from the fluid 60. In another arrangement, as one example, the system 10 comprises a microorganism growing apparatus 12 which is capable of cultivating microorganisms 84 to remove a pollutant from a fluid 60.

Any type of microorganism 84 may be utilized in the system 10 or microorganism growing apparatus 12 without departing from the scope of the disclosure. In one arrangement, as one example, the microorganisms 84 may be bacteria or algae 52. Additionally, in one arrangement, the microorganisms 84 may be fungi. Furthermore, in one arrangement, as one example, biofilm based microorganisms ("a microorganism biofilm") may be utilized. A microorganism biofilm may also be referred to as a "microbial biofilm", a "harvestable microbial biofilm", or a "biofilm" without departing from the scope of the disclosure. Alternatively, in another arrangement, as an example, suspended microorganism systems may be utilized without departing from the scope of the disclosure.

Algae

The system 10 and microorganism growing apparatus 12 are capable of using algae 52 as the microorganism 84 to remove a pollutant from a fluid 60. In one arrangement, the system 10 is capable of removing pollutants from a fluid 60 by providing a moving bed biofilm reactor 10 having a reservoir 42 wherein the reservoir 42 contains a fluid 60 and wherein the fluid 60 contains nutrients conducive to microorganism 84 growth; providing one or more inert biomass carriers 116 having a surface area configured to support growth of the microorganisms 84; exposing at least a portion of the carriers 116 to the microorganisms 84; submerging the carriers 116 in the fluid 60; and controlling a condition 64 of the fluid 60. In another arrangement, the system 10 and microorganism growing apparatus 12 are capable of removing pollutants from a fluid 60 by providing a first reservoir 42, filling the first reservoir 42 with a first fluid 58; controlling the first fluid 58 within the first reservoir 42 to have a first condition 64 that is conducive to growing algae 52; growing algae 52 using the microorganism growing apparatus 12, exposing the algae 52 to the first fluid 58 within the first reservoir 42 wherein the algae 52 are exposed to the first condition 64, providing a second reservoir 44, filling the second reservoir 44 with a second fluid 60 having a concentration of a pollutant; controlling the second fluid 60 within the second reservoir 44 to have a second condition 66; exposing a portion of the algae 52 to the second fluid 60 within the second reservoir 44 wherein the algae 52 are exposed to the second condition 66 and the algae 52 consume or uptake the pollutant from the second fluid 60; exposing the algae 52 to light 50 and air 48, and providing a third reservoir 46, filling the third reservoir 46 with a third fluid 62; controlling the third fluid 62 within the third reservoir 46 to have a third condition 68; exposing a portion of the algae 52 to the third fluid 62 within the third reservoir 46 wherein the algae 52 are exposed to the third condition 68 and the algae 52 are stimulated to release the pollutant into the third fluid 62.

Any species or type of algae 52 may be utilized in the system 10 without departing from the scope of the disclosure. In one arrangement, as one example, the algae 52 may be *Chlorella* algae or *Spirulina* algae. Additionally, in one arrangement, the algae 52 may be of the type regarded as Generally Regarded As Safe.

As stated above, any type of algae 52 may be utilized in the microorganism growing apparatus 12. In one arrangement, as one example, biofilm based algae ("an algae biofilm") may be utilized. Alternatively, in another arrangement, as one example, suspended algal culture systems may also be utilized without departing from the scope of the disclosure.

In one arrangement, as one example, the algae 52 contains extracellular polymeric substances which enhance absorption of pollutants, including, but not limited to, phosphorous, by the algae 52. Additionally, in one arrangement, the algae 52 contains extracellular polymeric substances which protect the algae 52 from toxic effects of high concentrations of pollutants, such as phosphorous.

Pollutant

The system 10 provides a method of using microorganisms 84 to remove a pollutant from a fluid 60. The pollutant may be in any form without departing from the scope of the disclosure. In one arrangement, as one example, the pollutant may be dissolved within the fluid 60. Any type of pollutant may be removed from the fluid 60 without departing from the scope of the disclosure. In one arrangement, as one example, the pollutant is Nitrogen (N), Phosphorous (P), Potassium (K), Carbon (C), ammonia ($NH_3$), carbon dioxide ($CO_2$), toxic metals, salts, pharmaceuticals, and/or hormones. Furthermore, any number of pollutants may be within the fluid 60. For example, the fluid 60 may comprise one pollutant, two pollutants, three pollutants, etc. without departing from the scope of the disclosure. In other words, the fluid 60 may comprise multiple types of pollutants without departing from the scope of the disclosure. In one arrangement, as one example, the fluid 60 may comprise all or some of the following types of pollutants: Nitrogen (N), Phosphorous (P), Potassium (K), Carbon (C), ammonia ($NH_3$), carbon dioxide ($CO_2$), toxic metals, salts, pharmaceuticals, and/or hormones.

Microorganism Growing Apparatus

As stated above, the system 10 may comprise a microorganism growing apparatus 12. A microorganism growing apparatus 12 is formed of any suitable size, shape, and design and is configured to grow any type of microorganism 84 including, but not limited to, algae 52. The microorganism growing apparatus 12 is configured to grow microorganisms 84 in any form without departing from the scope of the disclosure. In one arrangement, as one example, the microorganism growing apparatus 12 is configured to grow algae 52 on the surfaces of a plurality of carriers 116. In the arrangement shown, as one example, for purposes of clarity, the microorganism growing apparatus 12 has a top 20, and a bottom 22. Further description of a microorganism growing apparatus can be found in U.S. Pat. No. 9,932,549 and U.S. application Ser. No. 16/774,168, which are hereby incorporated by reference in its entirety.

As shown in FIG. 1, in one arrangement, as one example, the system 10 comprises a microorganism growing apparatus 12 wherein microorganisms 84 such as bacteria, algae 52, and the like are cultivated. The microorganism growing apparatus 12 is formed of a first basin or first reservoir 42 (or simply a "reservoir 42") containing inert biomass carriers 116. The carriers 116 are exposed to a first fluid 58 within the reservoir 42. In one embodiment, the reservoir 42 may contain a first fluid 58 (or simply a "fluid") that contains nutrients necessary for the successful cultivation of microorganisms 84, a CO2-rich gaseous phase 48 (also referred to as "air" throughout the disclosure), and light 50 (also referred to as a "sunlight capture" part throughout the disclosure). Submerged in fluid 58 are one or more carriers 116 on which microorganisms 84 grow and may be moved from one part of the system 10 to another part. In another embodiment, carriers 116 may be exposed to fluid 58 and nutrients by spraying fluid 58 and nutrients on carriers 116 that are resting within the reservoir 42.

The microorganism growing apparatus 12 may also include additional components, such as, a pump 82. Any type or form of microorganism growing apparatus 12 may be utilized in the system 10, including, but not limited to, horizontal stationary sheets with microorganisms 84 growing on the surface, vertical stationary sheets with microorganisms 84 growing on the surface, rotating drums with microorganisms 84 growing on the surface, carriers 116 which may take the form of small floating beads, small cylinders, or another solid media with microorganisms 84 growing on their surface without departing from the scope of the disclosure. In the case of carriers 116, algae predominantly grows on the biomass carriers within the fluid 58/60/62.

In one arrangement, as shown, the microorganism growing apparatus 12 comprises a plurality of reservoirs 42/44/46. For example, in one arrangement, the microorganism growing apparatus 12 comprises a first reservoir 42 and a second reservoir 44. In another arrangement, as shown, the microorganism growing apparatus 12 comprises a first reservoir 42, a second reservoir 44, and a third reservoir 46. Any type or form of reservoirs 42/44/46 may be utilized in the microorganism growing apparatus 12 without departing from the scope of the disclosure. Any number of reservoirs 42/44/46 may be utilized in the microorganism growing apparatus 12 without departing from the scope of the disclosure.

As stated above, the microorganism growing apparatus 12 comprises at least one reservoir 42/44/46, among other components. Reservoir 42/44/46 is formed of any suitable size, shape, and design and is configured to support the microorganism growing apparatus 12 and contain a fluid 58/60/62. In one arrangement, as one example, reservoir 42/44/46 is circular, square, or rectangular in shape. However, any other shape or configuration is hereby contemplated for use. Furthermore, the reservoir 42/44/46, and the microorganism growing apparatus 12, may be any size without departing from the disclosure. The reservoir 42/44/46, and the microorganism growing apparatus 12, may be manufactured to be small enough to fit on a shelf for research purposes and the like, or large enough to efficiently and effectively serve a large metropolitan city. Reservoir 42/44/46 may be formed of any type of reservoir 42/44/46 configured to contain carriers 116. In one embodiment, reservoir 42/44/46 may be a container configured to contain a fluid 58/60/62 including, but not limited to, a plastic tub or tote or a trough system. In another embodiment, carriers 116 may be exposed to fluid 58/60/62 and nutrients by spraying fluid 58/60/62 and nutrients on carriers 116 that are resting within the reservoir 42/44/46.

In one arrangement, as shown the microorganism growing apparatus 12 comprises a first reservoir 42, among other components. In another arrangement, as shown, the microorganism growing apparatus 12 comprises a first reservoir 42 and a second reservoir 44, among other components. In another arrangement, as shown, the microorganism growing apparatus 12 comprises a first reservoir 42, a second reservoir 44, and a third reservoir 46. Any number of reservoirs 42/44/46 may be utilized by the microorganism growing apparatus 12 without departing from the scope of the disclosure. For example, the microorganism growing apparatus 12 may comprise one, two, three, four, five, six, seven, eight, nine, ten, or more reservoirs 42/44/46 without departing from the scope of the disclosure. Throughout the disclosure, reference to a reservoir 42/44/46 refers to a first reservoir 42, a second reservoir 44, or a third reservoir 46; unless the disclosure specifically states that it is referring to only one of the reservoirs 42/44/46.

The microorganism growing apparatus 12 may also comprise a mechanism for creating inertia within the reservoir 42/44/46, thus creating movement of carriers 116 within the reservoir 42/44/46. Such a mechanism may comprise a mixing arm. Alternatively, inertia or movement of carriers 116 within the reservoir 42/44/46 may be created by shaking, tilting or pumping a fluid into reservoir 42/44/46. Such movement of carriers 116 may be desirable if carriers 116 have become trapped in a fixed or stationary state resting above or buoyant on the fluid 58/60/62 or sunken below the fluid 58/60/62. When this happens, carriers 116 may be allowed to remain in such a fixed or stationary state, or carriers 116 may be moved by operation of the mechanism for creating inertia or movement. Movement of carriers 116 within the reservoir 42/44/46 is important as movement toward and away from light and interaction with other carriers 116 impacts growth of microorganisms 84. Contact and interaction between carriers 116 causes sloughing off of microorganisms 84 from one carrier 116 to another, thus encouraging the spread of microorganisms 84 between carriers 116 and further encouraging growth of microorganisms 84.

Reservoir

A first reservoir 42 is designed to contain or hold carriers 116, and may be designed to contain the first fluid 58 which contains nutrients conducive to the cultivation of microorganisms 84. Carriers 116 are exposed to microorganisms 84 and may be submerged in first fluid 58, or alternatively carriers may be exposed to the first fluid 58 and nutrients by another means such as spraying the first fluid 58 and nutrients onto carriers 116 resting within the first reservoir 42. The first reservoir 42 may be open at its top 20 such that the surface of fluid 58 and at least a portion of the carriers 116 are exposed to air 48 and light 50. The carriers 116 and/or first fluid 58 contained within the first reservoir 42 are maintained at a first condition 64 that is conducive to cultivation of microorganisms 84. Through exposure of carriers 116 to fluid 58 under a first condition 64 in the presence of nutrients conducive to the growth of microorganisms 84, microorganisms 84 are allowed to grow and reproduce on the surfaces of carriers 116.

The second reservoir 44 is designed to contain or hold carriers 116, and may be designed to contain the second fluid 60 which contains a pollutant. The second reservoir 44 and the third reservoir 46 may be located within or near the first reservoir 42. A portion of the carriers 116 containing microorganisms 84 may be moved from other parts of the system 10 to second reservoir 44 where they are exposed to pollutant. The second reservoir 44 may be open at its top 20 such that the surface of fluid 60 and at least a portion of the carriers 116 are exposed to air 48 and light 50. The carriers 116 and/or second fluid 60 contained within the second reservoir 44 are maintained at a second condition 66 that induces the microorganisms 84 contained on carriers 116 to consume or uptake pollutant. Through exposure of carriers 116 containing microorganisms 84 to fluid 60 under the second condition 66, the microorganisms 84 are allowed to consume or uptake the pollutant.

The third reservoir 46 is designed to contain or hold carriers 116, and may be designed to contain the third fluid 62 which provides conditions favorable for the release of pollutant and contains released pollutant. The second reservoir 44 and the third reservoir 46 may be located within or near the first reservoir 42. A portion of the carriers 116 containing microorganisms 84 may be moved from other parts of the system 10 to third reservoir 46 where they are induced to release pollutant. The third reservoir 46 may be open at its top 20 such that the surface of fluid 62 and/or at least a portion of the carriers 116 are exposed to air 48 and light 50. The carriers 116 and/or third fluid 62 contained within the third reservoir 46 are maintained at a third condition 68 that induces the microorganisms 84 contained on carriers 116 to release pollutant. Through exposure of carriers 116 containing microorganisms 84 to fluid 62 under the third condition 68, the microorganisms 84 are allowed to release the pollutant.

In one arrangement, as one example, reservoir 42/44/46 may also include a pump 82 which is configured to circulate fluid 58/60/62 within reservoir 42/44/46. The circulation of the fluid 58/60/62 within reservoir 42/44/46 may improve the growth of the microorganisms 84 and the efficiency of the microorganism growing apparatus 12 and system 10. As described in more detail below, pump 82 may be any type of pump 82 such as a paddlewheel.

Pump

The microorganism growing apparatus 12 may comprise, in addition to other components, a pump 82. The pump 82 is formed of any suitable size, shape, and design and is configured to facilitate the movement of water through the system 10. In the arrangement shown, as one example, pump 82 is one or more electric pumps 82, however, any configuration of a pump 82 or pumping system 82 is hereby contemplated for use. Pump 82 may be formed of any size without departing from the disclosure.

Pump 82 is configured to circulate fluid 58 within the first reservoir 42 which may improve the growth of algae 52 and the efficiency of the microorganism growing apparatus 12. Pump 82 can be any type of pump 82 including, but not limited to, an electric pump, a wheel, a paddlewheel or any other type of pump 82 that is configured to circulate fluid 58.

Light Source

A light source 118 is designed to provide desired light conditions in a reservoir 42/44/46. Light source 118 may comprise a lamp suspended above a reservoir 42/44/46 and positioned such that light 50 produced by light source 118 is directed into the reservoir 42/44/46. Any type of lamp using any wavelength of light 50 may be used as a light source 118 without departing from the disclosure. Alternatively, light source 118 may comprise ambient light available in the environment in which the microorganism growing apparatus 12 is located. In one embodiment, light source 118 comprises a combination of natural and artificial light that is photosynthetically active light, where photosynthetically active light refers to the range of visible light that plants can use for photosynthesis (typically having wavelength values within the range of 400 to 700 nm).

Temperature Control Mechanism

A temperature control mechanism 120 is designed to provide desired temperature conditions in a reservoir 42/44/46. Temperature control mechanism 120 may comprise a heat lamp suspended above reservoir 42/44/46 and positioned such that the fluid 58/60/62 in the reservoir 42/44/46 is maintained at a desired temperature. Any type of device capable of heating, cooling, or otherwise maintaining a desired temperature may be used as a temperature control mechanism 120 without departing from the disclosure. Alternatively, temperature control mechanism 120 may comprise a submersible heater submerged in fluid 58/60/62.

Inlet

Fluid 58/60/62 enters reservoir 42/44/46 via an inlet 90. The inlet 90 may be located at any position on the outer perimeter of the reservoir 42/44/46 without departing from the scope of the disclosure. As previously stated, the system 10 comprises, among other components, a fluid recirculation system. The inlet 90 is connected to at least one of the fluid recirculation system which allows fluid 58/60/62 to flow into the reservoir 42/44/46. The inlet 90 may be formed of any suitable size, shape, and design. Furthermore, the inlet 90 may be formed of any material that is acceptable for entry of a fluid 58/60/62. In one arrangement, as one example, the inlet 90 is formed of a fluid recirculation system, a tube, a filter, a mesh filter, etc. The inlet 90 may be formed of any material without departing from the scope of the disclosure.

Center Drain

A center drain 92 disposed in the bottom 22 of a reservoir 42/44/46 allows fluid 58/60/62 to exit the reservoir 42/44/46 through the center of the reservoir 42/44/46. Center drain 92 may be closed or a stopper may be inserted into center drain 92 to prevent fluid 58/60/62 from exiting reservoir 42/44/46, and center drain 92 may be opened or a stopper may be removed to allow fluid 58/60/62 to exit reservoir 42/44/46. The center drain 92 may be formed of any material that is acceptable for a fluid 58/60/62 to exit a reservoir 42/44/46. Furthermore, the center drain 92 may be formed of any material that is acceptable for a fluid 58/60/62 to exit a reservoir 42/44/46. The center drain 92 may be formed of any material without departing from the scope of the disclosure.

Sieve

A sieve 122 covers center drain 92 and prevents carriers 116 from exiting reservoir 42/44/46 when fluid 58/60/62 is drained from reservoir 42/44/46. Sieve 122 may comprise a screen, mesh, grate, or any other material that prevents carriers 116 from exiting through center drain 92.

Mechanized Harvesting System

As provided above, the microorganism growing apparatus 12 may comprise, among other components, a mechanized harvesting system. The mechanized harvesting system comprises at least one moving belt, among other components. The belt may be provided to move microorganisms 84 between the reservoirs 42/44/46 and to provide additional surface area on which microorganisms 84 can grow. The at least one moving belt is formed of any suitable size, shape, and design. The at least one moving belt may be formed of any material without departing from the scope of the disclosure. The at least one belt may be formed of any type of material, including, but not limited to, plastic, metal, non-metal materials, rubber, polyvinyl chloride (PVC), or any other type of material. Furthermore, the at least one moving belt may be referred to as a belt, at least one moving belt, at least one belt, etc. without departing from the disclosure.

In one arrangement, as one example, the at least one belt is controlled by a motor, a gear system and at least one drive shaft wherein the at least one drive shaft rotates the at least one moving belt. The rotation of the at least one moving belt allows the at least one moving belt to move through and between the reservoirs 42/44/46 wherein the at least one moving belt is transitioned between a submerged position in which the belt is submerged in a fluid 58/60/62 and an exposed position wherein a portion of the at least one moving belt is not submerged in a fluid 58/60/62. In another arrangement, the at least one moving belt moves through the microorganism growing apparatus 12 wherein the at least one moving belt is transitioned between a submerged position wherein a portion of the at least one moving belt is submerged within the first fluid 58 held within the first reservoir 42, then to an exposed position wherein a portion of the at least one moving belt is not submerged within the first fluid 58 held within the first reservoir 42, then the at least one moving belt moves to a second submerged position wherein a portion of the at least one moving belt is submerged within the second fluid 60 held within the second reservoir 44, then to an exposed position wherein a portion of the at least one moving belt is not submerged within the second fluid 60 held within the second reservoir 44, then the at least one moving belt moves to a third submerged position 74 wherein a portion of the at least one moving belt is submerged within the third fluid 62 held within the third reservoir 46.

The at least one moving belt may move through the microorganism growing apparatus 12 in any type of configuration or movement without departing from the scope of the disclosure. In one arrangement, as one example, the at least one belt moves through the microorganism growing apparatus 12 in a continuous manner or loop between the reservoirs 42/44/46.

In an alternative arrangement, the at least one belt moves in a serpentine manner between submerged and exposed positions. Furthermore, the at least one moving belt may move through the microorganism growing apparatus 12 in any direction or configuration, including, but not limited to, horizontal, vertical, downward, upward, etc. without departing from the scope of the disclosure. In one arrangement, as shown, the at least one moving belt moves through the microorganism growing apparatus 12 in a substantially vertical configuration.

The at least one moving belt may comprise a coating on the at least one moving belt that is capable of binding pollutants. The coating may be comprised of any type of material, including, but not limited to, coatings that create temporary ionic, covalent, polar, or hydrogen bonds with a pollutant, or any other type of material. Furthermore, any amount of the coating may be utilized on the at least one moving belt without departing from the disclosure.

As the at least one moving belt moves through the microorganism growing apparatus 12, microorganisms 84 grow on the at least one moving belt. The microorganisms 84 that are produced may be harvested or removed from the at least one moving belt. The microorganisms 84 may be removed from the at least one moving belt by utilizing any method without departing from the scope of the disclosure. In one arrangement, as one example, the microorganisms 84 may be removed from the at least one moving belt by spraying, scraping, vibration, use of a pneumatic tool or apparatus, a pneumatic process, and the like. One method of harvesting the microorganisms 84 that are produced is to scrape the microorganisms 84 off of the at least one moving belt. In one arrangement, the system 10 comprises the step of harvesting the microorganisms 84 by positioning a harvesting blade along the at least one moving belt in order to scrape the microorganisms 84 off of the at least one moving belt. Therefore, the mechanized harvesting system comprises a harvesting blade.

In one arrangement, as one example, as the at least one moving belt moves through the microorganism growing apparatus 12, algae 52 grows in a biofilm which forms on the at least one moving belt. The algae 52 that is produced must be harvested or removed from the at least one moving belt. The algae 52 may be harvested or removed from the at least one moving belt by utilizing any method without departing from the scope of the disclosure. One method of harvesting the algae 52 that is produced is to scrape the algae 52 off of the at least one moving belt. In one arrangement, the system 10 comprises the step of harvesting the algae 52 by positioning a harvesting blade along the at least one moving belt in order to scrape the algae 52 off of the at least one moving belt.

The harvesting blade is formed of any suitable size, shape, and design. The harvesting blade may be formed of any material that is suitable for harvesting or removing microorganisms 84 from the at least one moving belt, such as a squeegee, a piece of plastic, a piece of rubber, a piece of metal, or the like. The harvesting blade may be formed of any material without departing from the scope of the disclosure.

The mechanized harvesting system may comprise, among other components, a harvesting reservoir. The harvesting reservoir may be formed of any suitable size, shape, and design. Furthermore, the harvesting reservoir may be formed of any material that is suitable for accepting and storing microorganisms 84. The harvesting reservoir may be formed of any material without departing from the scope of the disclosure. The harvesting reservoir may be connected to the harvesting blade or positioned next to the harvesting blade and is configured to receive the microorganisms 84 as the microorganisms 84 are harvested from the at least one moving belt.

Fluid

As stated above, the microorganism growing apparatus 12 comprises at least one fluid 58/60/62, among other components. The fluid 58/60/62 may be any type of fluid 58/60/62, including, but not limited to, water, wastewater, effluent, and the like. In one arrangement, the fluid 58/60/62 may be the fluid 58/60/62 utilized in a system which contains a concentration of pollutants including, but not limited to, N, P, K, C, ammonia (NH3), carbon dioxide (CO2), metals, salts, pharmaceuticals or hormones. In another arrangement, as one example, the fluid 58/60/62 is effluent from a feed manufacturer which contains a high concentration of pollutants including, but not limited to, N, P, K, C, toxic metals, salts, pharmaceuticals or hormones. Furthermore, in another arrangement, as one example, the fluid 58/60/62 is municipal water which contains a high concentration of pollutants including, but not limited to, N, P, K, C, toxic metals, salts, pharmaceuticals or hormones.

Conditions

As stated above, the microorganism growing apparatus 12 comprises at least one fluid 58/60/62, among other components, wherein the fluid 58/60/62 is controlled to have a condition 64/66/68. The condition 64/66/68 may be any type of condition 64/66/68 without departing from the scope of the disclosure. For example, the condition 64/66/68 may be an elevated temperature, an elevated temperature compared to another condition 64/66/68 used within the microorganism growing apparatus 12, an elevated temperature within the range of 30-90 degrees Celsius, an illumination using increased light intensity, exposure to a sorbent material, exposure to a phosphorous absorbing material, exposure to a fluid with a high concentration of biological oxygen demand, among other types of conditions 64/66/68 that stimulate algae 52 to release a pollutant. The microorganism growing apparatus 12 may comprise any number of reservoirs 42/44/46, fluids 58/60/62, and conditions 64/66/68 without departing from the scope of the disclosure. Therefore, the microorganism growing apparatus 12 may comprise one, two, three, four, five, six, seven, eight, nine, ten, or more reservoirs 42/44/46, fluids 58/60/62, and conditions 64/66/68 without departing from the scope of the disclosure. Throughout the disclosure, reference to a reservoir 42/44/46 refers to a first reservoir 42, a second reservoir 44, or a third reservoir 46, unless the disclosure specifically states that it is referring to only a specific reservoir 42/44/46. Throughout the disclosure, reference to a fluid 58/60/62 refers to a first fluid 58, a second fluid 60, or a third fluid 62, unless the disclosure specifically states that it is referring to only a specific fluid 58/60/62. Throughout the disclosure, reference to a condition 64/66/68 refers to a first condition 64, a second condition 66, or a third condition 68, unless the disclosure specifically states that it is referring to only a specific condition 64/66/68.

The condition 64/66/68 may be a temperature condition that is conducive to the growth of microorganisms 84. For example, a temperature within the range of 13° C.-30° C. is conducive to the growth of algae 52. The condition 64/66/68 may be a light condition conducive to the growth of microorganisms. For example, the condition 64/66/68 may refer to constant (24 hours per day, 7 days per week) exposure to grow lights. In another example, the condition 64/66/68 may refer to a mixture of lighting conditions where inert carriers 116 on which algae 52 is growing may are moved to and away from light source 118.

In Operation

In one arrangement, as one example, the system 10 provides for production of microorganism biomass comprising a reservoir 42 configured to contain a fluid 60 wherein the fluid provides nutrients to microorganisms 84 and one or more inert biomass carriers 116 having a surface area configured to support growth of the microorganisms 84.

In one arrangement, as one example, the system 10 comprises utilizing a microorganism growing apparatus 12 in a system 10 in cultivate microorganisms 84 such as algae 52 in order to filter a fluid 60 utilized in the system 10 to treat a fluid 60 or to provide for rearing of aquatic animals and/or cultivation of aquatic plants. Here, the system 10 comprises the steps of: filing a plurality of tanks 88 with a fluid 58/60/62; moving the fluid 58/60/62 from the plurality of tanks 88 through either the center drain 92 or the sidewall drain 94 of each tank 88 to a first header tank via a fluid recirculation system; moving the fluid 58/60/62 from the first header tank to the drum filter; moving the fluid 58/60/62 from the drum filter to the microorganism growing apparatus 12 via a waterfall; utilizing the microorganism growing apparatus 12 to grow microorganisms 84 and filter the fluid 58/60/62.

Growing microorganisms using a microorganism growing apparatus 12 may comprise the steps of: providing a first reservoir 42, filling the first reservoir 42 with a first fluid 58, submerging a plurality of carriers 84 in the first fluid 58 wherein at least a portion of the carriers 116 have been exposed to microorganisms 84, controlling the first fluid 58 within the first reservoir 42 to have a first condition 64 that is conducive to growing microorganisms 84, exposing the microorganisms 84 to the first fluid 58 within the first reservoir 42 wherein the microorganisms 84 are exposed to the first condition 64 and the microorganisms 84 grow, providing a second reservoir 44, filling the second reservoir 44 with a second fluid 60 having a concentration of a pollutant; controlling the second fluid 60 within the second reservoir 44 to have a second condition 66; exposing a portion of the microorganisms 84 to the second fluid 60 within the second reservoir 44 wherein the microorganisms 84 are exposed to the second condition 66 and the microorganisms 84 consume or uptake the pollutant from the second fluid 60, providing a third reservoir 46, filling the third reservoir 46 with a third fluid 62, controlling the third fluid 62 within the third reservoir 46 to have a third condition 68, and exposing a portion of the microorganisms 84 to the third fluid 62 within the third reservoir 46 wherein the microorganisms 84 are exposed to the third condition 68 and the microorganisms 84 are stimulated to release the pollutant into the third fluid 62.

Controlling a condition 64/66/68 may comprise controlling the temperature of the air 48 within a reservoir 42/44/46, controlling the temperature of a fluid 58/60/62 within a reservoir 42/44/46, and/or controlling the light 50 within a reservoir 42/44/46 in order to facilitate growth of the microorganisms 84, induce consumption or intake of a pollutant, or induce release of a pollutant. Additionally, in one arrangement, as one example, the system 10 further comprises the step of harvesting the microorganisms 84 and using the harvested microorganisms 84 as a foodstuff for human or non-human animal consumption, a fertilizer, a bioplastic, and/or a biofuel.

In order to introduce microorganisms 84 to a particular reservoir 42/44/46, fluid 58/60/62, or condition 64/66/68, carriers 116 on which the microorganisms 84 have grown must be physically transferred from one reservoir 42/44/46 to another reservoir 42/44/46. Carriers 116 containing microorganisms 84 may be transferred by manually straining carriers 116 out of a fluid 58/60/62 contained in one reservoir 42/44/46 and placing them into another reservoir 42/44/46. Alternatively or additionally, microorganisms 84 that have fallen off of the carriers 116 as a result of the motion of fluid 58/60/62 may be strained from the fluid 58/60/62 and manually placed in another reservoir 42/44/46. Alternatively or additionally, microorganisms 84 may be transferred between reservoirs 42/44/46 by a moving belt that travels between reservoirs 42/44/46 and provides additional surface area on which microorganisms 84 can grow.

In one arrangement, the microorganism growing apparatus 12 further comprises the step of: following release of the pollutant, the microorganisms 84 are then brought back to the second reservoir 44 to uptake additional pollutants and the process is repeated. Furthermore, in one arrangement, as one example, the microorganism growing apparatus 12 further comprises the step of: starving the microorganisms 84 of the pollutant by exposing the microorganisms 84 to the second condition 66 thereby causing the microorganisms 84 to consume increased amounts of the pollutant from the second fluid 60 in the second reservoir 44. In one arrangement, as one example, the system 10 comprises concentrating the pollutant within the second fluid 60 held within the second reservoir 44. In one example, the microorganism growing apparatus 12 grows the microorganisms 84 on a belt wherein the belt moves in a continuous manner through the reservoirs 42/44/46.

After the fluid 58/60/62 has moved throughout the microorganism growing apparatus 12, the fluid 58/60/62 transitions to the sump pump; then the fluid 58/60/62 moves to the foam fractionator for additional filtering; then the fluid 58/60/62 moves to the LHO for additional filtering; eventually the fluid 58/60/62 moves to the second header tank and back to a tank 88 through the inlet 90 of the tank 88 where the cycle throughout the system 10 takes place again.

Additionally, the system 10 may further comprise a bacterial or chemical treatment of the fluid 58/60/62. The bacterial or chemical treatment of the fluid 58/60/62 may be any type of bacterial or chemical treatment including, but not limited to, chlorine, chlorine dioxide, algicide, and the like. However, any type of bacterial or chemical treatment of the fluid 58/60/62 may be utilized without departing from the disclosure.

Figure 3:
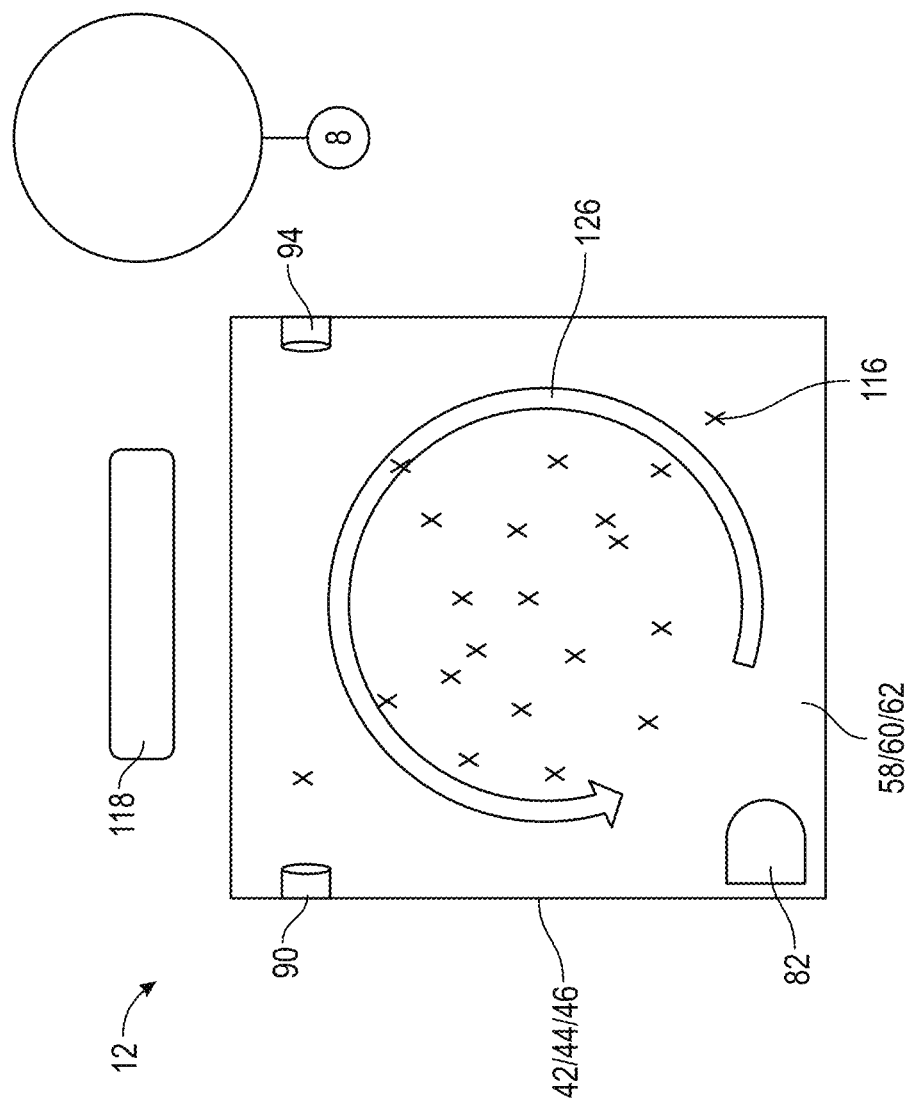
FIG. 3 depicts a hybrid micro-algal carrier reactor according to one embodiment.

Operation of the System 10 as Depicted in FIG. 3

In another arrangement, as depicted in FIG. 3, the system 10 is used for cultivation of immobilized micro-algae biofilm on the surface of inert carrier media 116 that is suspended in a fluid 58/60/62 contained in a reactor vessel 42/44/46. The immobilized micro-algae biofilm is used in a process for micro-algal 52 production and water treatment. The novel reactor 12 is a hybrid system that has biofilm attached to the inert carriers 116, and the biofilm detaches from the carriers 116 and enters a suspended phase.

Algae 52 biomass produced in microorganism growing apparatus 12 is for purposes including but not limited to, food, feed, fuel, and fiber. Algae 52 water treatment includes the positioning of microorganism growing apparatus 12 in systems for standalone biological treatment or pretreatment of a fluid 58/60/62. Algae 52 production and water treatment processes include the conversion of influent water nutrients into algae 52 biomass and processes of algae 52 respiration resulting in oxygenation/oxygen addition into fluid 58/60/62.

Carrier 116 and vessel 42/44/46 characteristics have an effect on the system's 10 nutrient removal capacity, filling fraction (concentration or density of carrier relative to vessel), microbial biocenosis (microbial community composition on carrier), and fouling propensity (algal cell accumulation amount and rate on carriers). Carrier 116 characteristics include, but are not limited to, carrier 116 geometry, dimensions, material composition, porosity, and surface texture. Any carrier 116 that has the ability to be buoyant or "free" in hydraulic flow in reactor vessel 42/44/46 and has the ability to accumulate algae biofilm that detaches into a suspended phase is suitable for use in microorganism growing apparatus 12. Carrier 116 characteristics also include carrier filling fraction and biofilm microbial biocenosis. A carrier 116 filling fraction of less than 70% fill has been found to provide favorable conditions for the growth of algae 52. A carrier 116 biofilm microbial biocenosis equal to or greater than 50% algae has been found to provide favorable conditions for the growth of algae 52.

As depicted in FIG. 3, the microorganism growing apparatus 12 comprises a reactor vessel 42/44/46, a fluid 58/60/62, nutrients contained in fluid 58/60/62, carriers 116, an inlet 90 for injection of fluid 58/60/62 into vessel 42/44/46, an outlet 94 for release of fluid 58/60/62 from vessel 42/44/46, a recirculation pump 82, a light source 118, and solids filter for removing solids from fluid 58/60/62.

Reactor vessel 42/44/46 characteristics include, but are not limited to, vessel 42/44/46 size, geometric design, and dimensions. Light source 118 characteristics include type of light, frequency, wavelength, amount of light 50, duration, dimensions, and proximity of light source 118 relative to vessel 42/44/46. Flow 126 characteristics include direction of flow 126, pattern of flow 126, and speed of flow 126. Pump 82 characteristics include type of pump 82. Solids filter characteristics include filter mechanisms, methodology, and flocculation agents and methodology. Harvesting characteristics include harvesting mechanism and methodology.

Use of a Fluidized Sand Bed for Cultivating Algae

Figure 4:
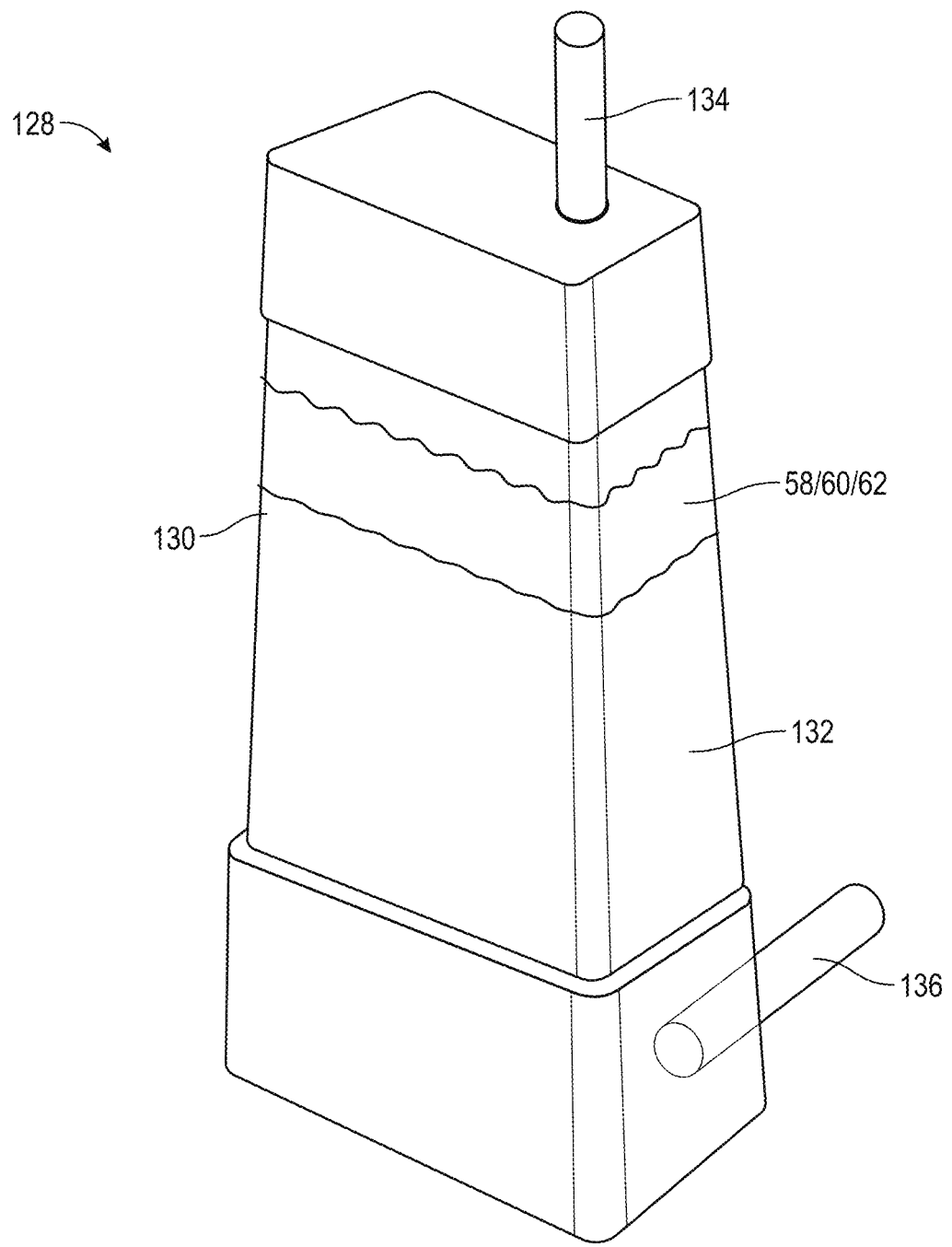
FIG. 4 depicts a perspective view of a bioreactor system using a fluidized sand filter to remove pollutants from a fluid according to one embodiment.

In another arrangement, as depicted in FIG. 4, a fluidized sand filter 128 may be used to cultivate microorganisms 84 as an alternative to cultivate microorganisms 84 in an MBBR system. A fluidized sand filter 128 may comprise a container 130 for holding a quantity of sand 132 and a fluid 58/60/62. An inlet 134 introduces unfiltered fluid 58/60/62 into the container 130 where the unfiltered fluid 58/60/62 passes through the sand 132 being held in the container 130. As the unfiltered fluid 58/60/62 passes through the sand 132, microorganisms 84 contained in the unfiltered fluid 58/60/62 attach to the sand 132, and the unfiltered fluid 58/60/62 is converted to a filtered fluid 58/60/62 through this filtration process. Filtered fluid 58/60/62 then passes out of container 130 via outlet 136. This filtration process occurs continuously as new unfiltered fluid 58/60/62 enters the container 130 through inlet 134, passes through sand 132, and exits through outlet 136. Additional microorganisms 84 attach to the sand 132 as the filtration process continues. The microorganisms 84 attached to the sand 132 are allowed to grow and reproduce, thereby microorganisms 84 are cultivated in fluidized sand filter 128.

The container 130 may be formed of any suitable size, shape, material, and color. In one arrangement, as one example, the container 130 may be clear to allow light 50 from an artificial or natural light source 118 to penetrate the container 130 and encourage the growth of microorganisms 84. Additionally or alternatively, the container 130 may be open to allow photosynthetic light 50 from an artificial or natural light source 118 to penetrate the container 130 and encourage growth of microorganisms 84.

Benefits of System

The system 10 has many benefits and advantages including, but not limited to, providing a method of using a microorganism 84 to remove a pollutant from a fluid 58/60/62 that is efficient; providing a method of using a microorganism 84 to remove a pollutant from a fluid 58/60/62 that is simple in design; providing a method of using a microorganism 84 to remove a pollutant from a fluid 58/60/62 that is inexpensive; providing a method of using a microorganism 84 to remove a pollutant from a fluid 58/60/62, harvesting the microorganism 84, and using the microorganism 84 as a foodstuff for human consumption; providing a method of using a microorganism 84 to remove a pollutant from a fluid 58/60/62, harvesting the microorganism 84, and using the microorganism 84 as a foodstuff for animal consumption; providing a method of using a microorganism 84 to remove a pollutant from a fluid 58/60/62 that is capable of meeting current pollutant discharge limits; providing a method of using a microorganism 84 to remove a pollutant from a fluid 58/60/62 that has a smaller footprint than other biological systems; providing a method of using a microorganism 84 to efficiently and effectively remove a pollutant from effluent; providing a method of using a microorganism 84 to remove a pollutant from a fluid 58/60/62 that has a high pollutant removal rate.

Furthermore, the system 10 provides a method to maximize production of aquatic animals and/or aquatic plants on a limited supply of water; providing a method to maximize production of aquatic animals and/or aquatic plants on a limited supply of land; providing a method to achieve disease control; providing a method to control the environment in order to maximize growth of aquatic animals and/or aquatic plants. These and other benefits and advantages of the system 10 are apparent from the specification and claims.

REFERENCE NUMERALS

- 10—A bioreactor system for production of microorganisms ("a system" or "a MBBR system")
- 12—Microorganism growing apparatus
- 20—A top (of the microorganism growing apparatus)
- 22—A bottom (of the microorganism growing apparatus)
- 42—A first reservoir
- 44—A second reservoir
- 46—A third reservoir
- 48—Air (a CO2-rich gaseous phase or an O2-rich gaseous phase)
- 50—Light (a "sunlight capture" part)
- 52—Algae
- 58—A first fluid
- 60—A second fluid
- 62—A third fluid
- 64—A first condition
- 66—A second condition
- 68—A third condition
- 82—A pump
- 84—Microorganism(s)
- 88—Plurality of tanks
- 90—Inlet (of tank)
- 92—Center drain (of tank)
- 94—Sidewall drain (of tank)
- 116—Carriers
- 118—Light source
- 120—Temperature control mechanism
- 122—Sieve
- 126—Flow
- 128—Fluidized sand filter
- 130—Container (of a fluidized sand filter)
- 132—sand
- 134—inlet (of a fluidized sand filter)
- 136—outlet (of a fluidized sand filter)

What is claimed is:

1. A method for cultivating photosynthetic microorganisms comprising:
   one or more tanks;
      the one or more tanks containing a first fluid and aquatic animals;
   a fluid recirculation system;
   a microorganism growing apparatus;
   wherein the microorganism growing apparatus is comprised of a first reservoir, a second reservoir, and microorganisms configured for removing one or more pollutants released by the aquatic animals;
   wherein the fluid recirculation system moves the first fluid from the one or more tanks to the first reservoir of the microorganism growing apparatus;
   wherein the first reservoir is configured to contain a plurality of inert biomass carriers, each inert biomass carrier having a surface area configured to support growth of the microorganisms;
   wherein, when the first fluid is moved to the first reservoir, the inert biomass carriers are exposed to the first fluid and nutrients within the first reservoir;
   wherein the first reservoir is exposed to a first condition conducive to the growth of the microorganisms and the microorganisms grow on the plurality of inert biomass carriers;
   wherein at least a portion of the plurality of inert biomass carriers containing the microorganisms are moved from the first reservoir to the second reservoir;
   wherein the second reservoir is configured to contain a second fluid which contains the one or more pollutants; and
   wherein the second reservoir is exposed to a second condition conducive to inducing the microorganisms to uptake the one or more pollutants, thereby removing the one or more pollutants from the second fluid.

2. The method of claim 1 wherein the first condition comprises providing a light source configured to control a light condition in the first reservoir.

3. The method of claim 2 wherein the light source produces photosynthetically active light.

4. The method of claim 1 wherein the first condition comprises providing a temperature control mechanism configured to control a temperature condition of the first fluid.

5. The method of claim 1 wherein the first condition comprises providing a mechanism configured to move the carriers from fixed positions above or below the first fluid.

6. The method of claim 1 wherein the one or more pollutants are selected from commercially available nutrient solutions, Nitrogen (N), Phosphorus (P), Potassium (K), Carbon (C), ammonia ($NH_3$), carbon dioxide ($CO_2$), metals, salts, pharmaceuticals or hormones.

7. The method of claim 1 wherein the material comprising the plurality of inert biomass carriers is a similar density to the first fluid.

8. The method of claim 1 wherein the first condition is comprised of the inert biomass carriers being in constant motion.

9. The method of claim 1 wherein the first condition is comprised of the inert biomass carriers being constantly exposed to Oxygen (O).

10. A method of cultivating photosynthetic microorganisms within a moving bed biofilm reactor comprising:
    one or more tanks;
       the one or more tanks containing a first fluid and aquatic animals;
    a fluid recirculation system;
    a microorganism growing apparatus;
    wherein the microorganism growing apparatus is comprised of a first reservoir, a second reservoir, and microorganisms configured for removing one or more pollutants released by the aquatic animals;
    wherein the fluid recirculation system moves the first fluid from the one or more tanks to the first reservoir of the microorganism growing apparatus;
    wherein the first reservoir of the moving bed biofilm reactor is configured to contain a plurality of inert biomass carriers having a surface area configured to support growth of the microorganisms;

wherein, when the first fluid is moved to the first reservoir, the inert biomass carriers are exposed to the first fluid and nutrients conducive to growth of the microorganisms;

wherein, to induce growth of the microorganisms, the carriers are periodically moved within the first reservoir;

wherein the microorganisms grow on the carriers;

wherein at least a portion of the carriers containing the microorganisms are moved from the first reservoir to the second reservoir;

wherein the second reservoir is configured to contain a second fluid which contains the one or more pollutants; and wherein the second reservoir is exposed to a second condition conducive to inducing the microorganisms to uptake the one or more pollutants, thereby removing the one or more pollutants from the second fluid.

11. The method of claim 10 further comprising controlling a light condition within the first reservoir.

12. The method of claim 10 further comprising controlling a nutrient composition and amount within the first reservoir.

13. The method of claim 10 wherein the microorganisms are photosynthetically active.

14. The method of claim 10 further comprising controlling movement of the carriers such that the carriers move toward and away from a light source.

15. The method of claim 10 further comprising controlling movement of the carriers such that the carriers come into contact with each other.

16. A method of cultivating photosynthetic microorganisms within a moving bed biofilm reactor comprising:
one or more tanks;
the one or more tanks containing a first fluid and aquatic animals;
a fluid recirculation system;
a microorganism growing apparatus;
wherein the microorganism growing apparatus is comprised of a first reservoir, a second reservoir, and microorganisms configured for removing one or more pollutants released by the aquatic animals;

wherein the fluid recirculation system moves the first fluid from the one or more tanks to the first reservoir of the microorganism growing apparatus;

wherein the first reservoir of the moving bed biofilm reactor is configured to contain a plurality of inert biomass carriers having a surface area configured to support growth of the microorganisms;

wherein, when the first fluid is moved to the first reservoir, the inert biomass carriers are exposed to the first fluid and nutrients conducive to growth of the microorganisms;

wherein, to induce growth of the microorganisms, the inert biomass carriers are exposed to a photosynthetic light source such that the photosynthetic microorganisms are exposed to a photosynthetic light condition;

wherein the microorganisms grow on the inert biomass carriers;

wherein at least a portion of the inert biomass carriers containing the microorganisms are moved from the first reservoir to the second reservoir;

wherein the second reservoir is configured to contain a second fluid which contains the one or more pollutants; and wherein the second reservoir is exposed to a second condition conducive to inducing the microorganisms to uptake the one or more pollutants, thereby removing the one or more pollutants from the second fluid.

17. The method of claim 16 further comprising controlling the photosynthetic light condition of the first fluid.

18. The method of claim 16 further comprising controlling a nutrient composition and amount within the first reservoir.

19. The method of claim 16 wherein the microorganisms are photosynthetically active.

20. The method of claim 16 further comprising controlling movement of the carriers such that the carriers move toward and away from the photosynthetic light source.

21. The method of claim 16 further comprising controlling movement of the carriers such that the carriers come into contact with each other.

\* \* \* \* \*